Feb. 10, 1948. A. F. WATKINS Plant Pat. 784
ROSE PLANT
Filed Nov. 12, 1946
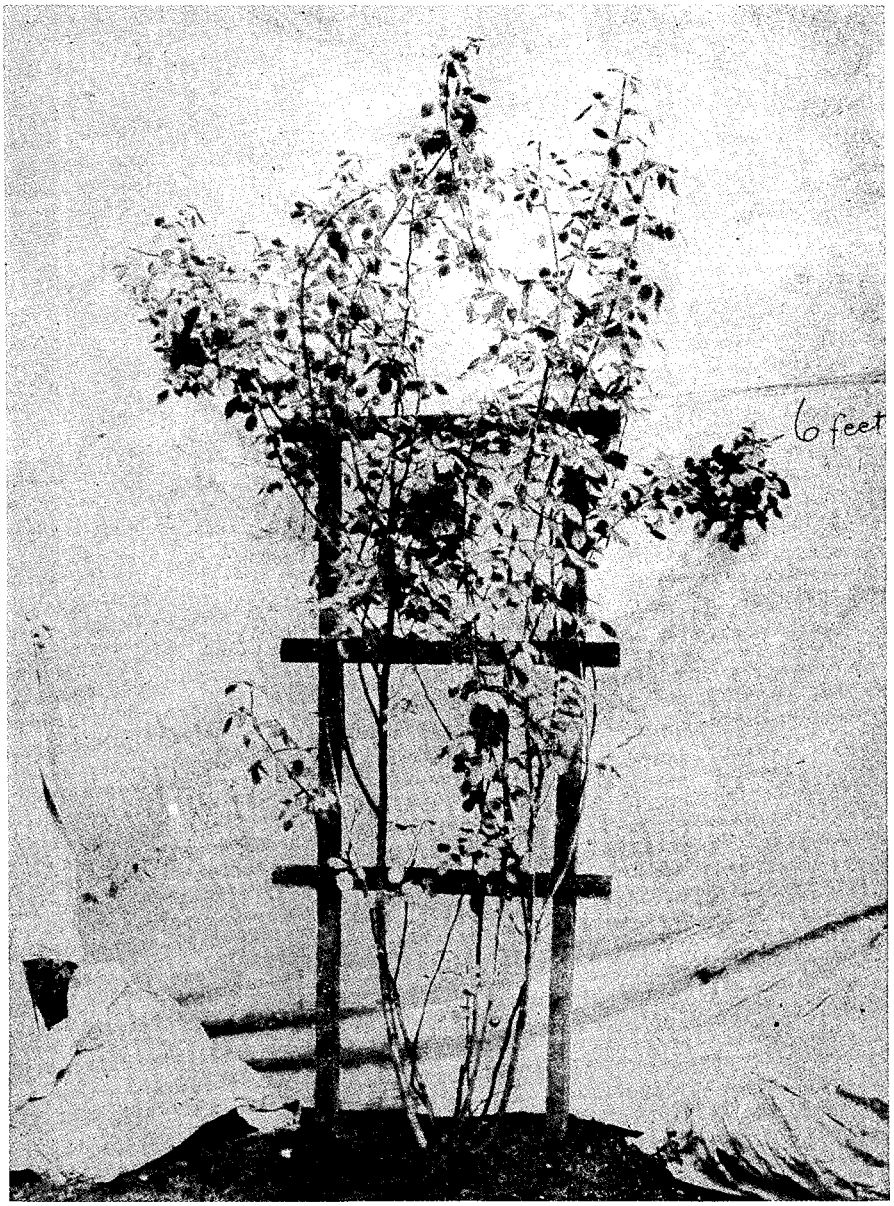
Inventor
A. F. Watkins
By Robb & Robb
Attorneys Patented Feb. 10, 1948

Plant Pat. 784

UNITED STATES PATENT OFFICE

784

ROSE PLANT

Archibald F. Watkins, Tyler, Tex., assignor to Krider Nurseries, Inc., Middlebury, Ind., a corporation of Indiana Application November 12, 1946, Serial No. 709,386

1 Claim. (Cl. 47—61)

The present discovery relates to a new and distinct variety of rose plant and is characterized primarily as to novelty by its vigorous climbing habit.

This new rose is a sport of the bush rose "Stratford" (Pl. Pat. No. 160), and was discovered by me growing in a nursery row of "Stratford" plants. In the development of the mother plant, careful observations of its characteristics disclosed that it resembled the bush plants in foliage, thorns, form and color of flowers, and other features, saving only the bush form.

The drawing illustrates a specimen of the plant and depicts its climbing habit.

By reference to the prior patent above mentioned, a full disclosure may be had of the present rose, except for its climbing habit, and it is believed unnecessary to repeat this description herein, particularly as rose "Stratford" has been extensively grown and disseminated especially in the South, and is, therefore, well known. The color of "Stratford" is particularly attractive, being a lustrous pink, heavily shaded with salmon and amber, and the blooms are full double, intensely fragrant and borne on long, straight stems.

These characteristics, as before stated, appear in this new climbing rose, and, therefore, enhance the value of the new rose because of the much greater attractive display produced in the larger form of plant.

More specifically, this new rose plant grows to a height of ten to fifteen feet, more than twice the normal growth of the "Stratford" bush, and asexual reproduction of the new variety shows this characteristic of climbing is established. By way of further confirmation of growth habit, I have now growing in the current nursery row, several hundred plants each, of the regular bush "Stratford" variety and this climbing form. At the very early stage of their growth, under such comparable conditions, the "Stratford" bush is about a foot high while the climbers are twice that height. As the plants develop, according to prior observations, this ratio increases materially.

In order to graphically show the climbing habit of this new variety, the accompanying drawing illustrates a specimen thereof held in its vertical position by means of a trellis which is indicated in the drawing to be a little more than six feet in height. It will be noted that this specimen has greatly exceeded the height of six feet and is growing to a still greater height as the age of the specimen increases.

I claim:

A new and distinct variety of rose plant of the hybrid tea class, characterized as to novelty by its vigorous climbing habit of growth and its similarity in other respects to its bush parent "Stratford," substantially as described and shown.

ARCHIBALD F. WATKINS.